United States Patent
Chen et al.

(10) Patent No.: US 11,830,600 B1
(45) Date of Patent: Nov. 28, 2023

(54) MOVEMENT ADJUSTMENT SYSTEM BASED ON HEART RATES AND RATING OF PERCEIVED EXERTION FEEDBACKS OF DIFFERENT USERS

(71) Applicant: Chengdu Shangyi Information Technology Co., Ltd., Chengdu (CN)

(72) Inventors: Xi Chen, Chengdu (CN); Guo Zhao, Chengdu (CN); Li Chen, Chengdu (CN); Ling Zeng, Chengdu (CN); Chunshui He, Chengdu (CN)

(73) Assignee: RPLUSHEALTH LIMITED, Cayman Islands (GB)

( * ) Notice: Subject to any disclaimer, the term of this patent is extended or adjusted under 35 U.S.C. 154(b) by 0 days.

(21) Appl. No.: 18/140,378

(22) Filed: Apr. 27, 2023

(30) Foreign Application Priority Data

May 17, 2022 (CN) .......................... 202210531450.8

(51) Int. Cl.
*G16H 20/30* (2018.01)
*G16H 10/60* (2018.01)
*G16H 80/00* (2018.01)

(52) U.S. Cl.
CPC ............. *G16H 20/30* (2018.01); *G16H 10/60* (2018.01); *G16H 80/00* (2018.01)

(58) Field of Classification Search
CPC ....................................................... G16H 20/30
See application file for complete search history.

(56) References Cited

U.S. PATENT DOCUMENTS

| 10,950,139 B1 * | 3/2021 | Lyke | ........................ G09B 5/00 |
| 2020/0281482 A1 * | 9/2020 | Watkins | ................... A61B 5/22 |

FOREIGN PATENT DOCUMENTS

| WO | WO-2010111767 A1 * | 10/2010 | ........... A61B 5/0205 |
| WO | WO-2020205276 A1 * | 10/2020 | ........... A61B 5/0205 |

* cited by examiner

*Primary Examiner* — Sheetal R Paulson
(74) *Attorney, Agent, or Firm* — Mark C. Johnson; Johnson Dalal

(57) ABSTRACT

A movement adjustment system based on heart rates and rating of perceived exertion (RPE) feedbacks of different users is provided, including: a user client, a heart rate monitoring device, a server, and a doctor client. The user client includes an RPE self-rating module, an RPE data acquisition module, a user-side video movement display module, and a user-side data storage module. The heart rate monitoring device includes an exercise data acquisition module. The server includes a data input module, a core processor, and a video movement library. The doctor client includes a doctor-side video movement display module, a video movement sending module, and a doctor-side data storage module. The above system according to the present disclosure adjusts, based on objective heart rate feedbacks during exercise and subjective RPE feedbacks after the exercise of different users, movements of next exercise of a patient.

7 Claims, 3 Drawing Sheets

MOVEMENT ADJUSTMENT SYSTEM BASED ON HEART RATES AND RATING OF PERCEIVED EXERTION FEEDBACKS OF DIFFERENT USERS

CROSS REFERENCE TO RELATED APPLICATION

This patent application claims the benefit and priority of Chinese Patent Application No. 202210531450.8 filed with the China National Intellectual Property Administration on May 17, 2022, the disclosure of which is incorporated by reference herein in its entirety as part of the present application.

TECHNICAL FIELD

The present disclosure relates to the field of healthcare informatics, and in particular, to a movement adjustment system based on heart rates and rating of perceived exertion (RPE) feedbacks of different users.

BACKGROUND

Exercise and fitness have gradually become an essential need in people's lives with improved living standards. Exercise is more critical for sub-healthy and chronic disease groups. Many scientific studies have confirmed that scientific and effective exercise can effectively improve sub-health conditions and improve cardiopulmonary endurance, especially for the three high (hyperglycemia, hyperlipidemia, and hypertension) disease state, and has a good therapeutic effect in blood sugar control, blood pressure and lipid reduction. Especially for the three high early patients, rational and scientific exercise has been recommended by domestic and international experts. However, in real life, most people do not reach an effective exercise range, or exercise excessively, which not only makes the effect of exercise significantly reduced, but also easily cause exercise injuries such as joint wear.

With the rapid development of electronic science and technology, the popularity of intelligent wearable device and mobile network provides a reliable basis for scientific and reasonable exercise health management. The existing intelligent wearable device can monitor some data of the user during exercise in real time, but it only records data and lack scientific and reasonable exercise feedback function, and cannot be used for exercise health management and need to be improved.

In the field of exercise physiology, reasonable aerobic exercise is considered to be an important indicator of the desired results of exercise and fitness. However, the strict definition of aerobic exercise needs to be judged by the indicators of blood biochemical detection, such as the level of blood lactic acid, which is not suitable for routine judgment in practice exercise. However, researchers have found in long-term practice that it is possible to simply judge whether an exerciser is in an aerobic exercise stage by understanding the heart rate during exercise. That is, there is a specific range of heart rate in the aerobic exercise state (aerobic exercise heart rate). If the exerciser's heart rate is maintained within this specific range for a certain period of time, the ideal effect of exercise can be obtained. A too low heart rate causes a poor fitness effect, and a too high heart rate poses a threat to health. In addition, due to different health conditions and physical conditions of persons, the range of their aerobic exercise heart rates will be different.

RPE is a theory established by the famous Swedish physiological psychologist Gunnar Borg in the 1970s. RPE is mainly aimed at adults and divides the exercise intensities into different levels from 1 to 10. "1" means no effort, "10" means extreme effort, and a usual range starts from "3". In exercise, the exercisers need to judge the ratings according to their own feelings, that is, the subjective feedback of the exerciser on the exercise intensity.

Therefore, how to intelligently adjust prescription movements of next exercise according to the heart rates of different users during exercise and the too high or too low RPE ratings after exercise, so as to make reasonable exercise prescription and achieve effective exercise is close to the actual demand, and is a technical problem that needs to be solved urgently in this field.

SUMMARY

An objective of embodiments of the present disclosure is to provide a movement adjustment system based on heart rates and RPE feedbacks of different users, which adjusts movements of next exercise of a patient based on objective heart rate feedback during exercise and subjective RPE feedback after the exercise of different users, such that movement recommendation of an exercise prescription is more accurate and reasonable, and the patient can exercise more safely and effectively through personalized adjustment of the movements.

To achieve the above objective, the present disclosure provides the following technical solutions.

A movement adjustment system based on heart rates and RPE feedbacks of different users, including:
a user client, a heart rate monitoring device, a server, and a doctor client, where
the user client includes an RPE data acquisition module, an RPE self-rating module, a user-side video movement display module, and a user-side data storage module; and the RPE data acquisition module, the RPE self-rating module, the user-side video movement display module, and the user-side data storage module are connected in sequence;
the heart rate monitoring device includes an exercise data acquisition module and is worn on a user; and the exercise data acquisition module is connected with the RPE self-rating module;
the server includes a data input module, a core processor, and a video movement library; and the input module is connected with the exercise data acquisition module and the core processor, and the core processor is connected with the video movement library;
the doctor client includes a doctor-side video movement display module, a video movement sending module, and a doctor-side data storage module; and the doctor-side video movement display module is connected with the exercise data acquisition module and the video movement sending module, and the video movement sending module is connected with the doctor-side data storage module.

Optionally, the RPE self-rating module is configured to rate difficulty of completing exercise after the exercise by the user;
the RPE data acquisition module is configured to acquire RPE rating information of the user;
the user-side video movement display module is configured to display exercise movements of the user;
the user-side data storage module is configured to store the exercise movements of the user.

Optionally, the exercise data acquisition module is configured to acquire heart rate information of the user during exercise; and the heart rate information includes a heart rate not reaching a lower limit of a target heart rate during exercise, a heart rate reaching a target heart rate range, and a heart rate exceeding an upper limit of the target heart rate.

Optionally, the data input module is configured to input the heart rate information and the RPE rating information of the user during exercise into the core processor; and the core processor is configured to select exercise movements suitable for the user from the video movement library according to the heart rate information and the RPE rating information of the user during exercise, replace movements not suitable for the user in an original exercise prescription, generate movements for a new exercise prescription, and send the movements for the new exercise prescription to the doctor client.

Optionally, the doctor-side video movement display module is configured to display video movements in the doctor client; and the video movement sending module is configured to send the video movements from the doctor client to the user client.

Optionally, the core processor specifically includes: a heart rate information processing sub-module, a duration recording sub-module, a too-high target heart rate processing sub-module, a too-low target heart rate processing sub-module. a too-high RPE rating processing sub-module, a too-low RPE rating processing sub-module, and a heart rate and RPE feedback collaborative processing sub-module;

the heart rate information processing sub-module is configured to process different exercise stages at which heart rate changes of the user during exercise are; the heart rate changes include not reaching a target heart rate, reaching the target heart rate, and exceeding the target heart rate; and the exercise stages include a warm-up exercise stage, a whole-body exercise stage, a cooling-down exercise stage, and a stretching exercise stage;

the duration recording sub-module is connected with the heart rate information processing sub-module, and the duration recording sub-module is configured to record durations of different exercise stages at which the heart rate changes of the user during exercise are; and the durations include durations of not reaching the target heart rate, reaching the target heart rate, and exceeding the target heart rate in the warm-up exercise stage, durations of not reaching the target heart rate, reaching the target heart rate, and exceeding the target heart rate in the whole-body exercise stage, durations of not reaching the target heart rate, reaching the target heart rate, and exceeding the target heart rate in the cooling-down exercise stage, and durations of not reaching the target heart rate, reaching the target heart rate, and exceeding the target heart rate in the stretching exercise stage;

the too-high target heart rate processing sob-module is connected with the heart rate information processing sub-module, and the too-high target heart rate processing sub-module is configured to adjust video movements in an exercise prescription of the user when a target heart rate of the user during exercise exceeds an upper limit of a target heart rate range;

the too-low target heart rate processing sub-module is connected with the heart rate information processing sub-module, and the too-low target heart rate processing sub-module is configured to adjust the video movements in the exercise prescription of the user when the target heart rate of the user during exercise is lower than a lower limit of the target heart rate range;

the too-high RPE rating processing sub-module is connected with the RPE self-rating module, the too-high RPE rating processing sub-module is configured to set an RPE rating standard value range (x,y) according to different user conditions, and when an RPE rating is greater than y after the user completes exercise once, a target heart rate range of a patient is decreased by X bpm; the different user conditions include an age, gender, and health status of the user, and the health status includes disease diagnosis and duration of illness;

the too-low RPE rating processing sub-module is connected with the RPE self-rating module, the too-low RPE rating processing sub-module is configured to set the RPE rating standard value range (x,y) according to different user conditions, and when the RPE rating is less than x after the user completes exercise once, the target heart rate range of the patient is increased by X bpm; the different user conditions include the age, gender, and health status of the user; and the health status includes disease diagnosis and duration of illness; and the heart rate and RPE feedback collaborative processing sub-module is connected with the too-low RPE rating processing sub-module and the too-high RPE rating processing sub-module, and the heart rate and RPE feedback collaborative processing sub-module is configured to adjust the video movements in the exercise prescription under simultaneous or non-simultaneous abnormalities of the heart rates and the RPE feedbacks of the different users during exercise; the simultaneous or non-simultaneous abnormalities include that the target heart rate being too high matches any one of RPE<x, x≤RPE≤y, and RPE>y, the target heart rate being within the target heart rate range matches any one of RPE<x, x≤RPE≤y, and RPE>y, and the target heart rate being too low matches any one of RPE<x, x≤RPE≤y, and RPE>y; after the user completes exercise once according to the video movements, when the target heart rate is abnormally too high or too low, the heart rate and RPE feedback collaborative processing sub-module performs processing according to a condition where the target heart rate is too high or too low; the processing includes transferring a processing task to the too-high target heart rate processing sub-module or the too-low target heart rate processing sub-module for processing, and an abnormal RPE feedback is not processed; the abnormal RPE feedback includes RPE<x or RPE>y; when the target heart rate is within the target heart rate range, and the RPE rating meets RPE<x or RPE>y, the heart rate and RPE feedback collaborative processing sub-module transfers a processing task to the too-low RPE rating processing sub-module or the too-high RPE rating processing sub-module for processing; and when the target heart rate is within the target heart rate range, and the RPE rating meets x≤RPE≤y, an exercise of the user is regarded as ideal, without movement adjustment being performed.

Optionally, determining the target heart rate of the user being higher than the upper limit of the target heart rate range includes that a duration of the target heart rate exceeding the upper limit of the target heart rate in a whole exercise stage and a total duration of the whole-body exercise are counted after the user completes exercise once according to the video movements, the duration of the target heart rate exceeding the upper limit of the target heart rate in the whole exercise stage is divided by the total duration of the whole-body exercise, and if a result is greater than X %, the system determines that the user has a target heart rate higher than the upper limit of the target heart rate range during exercise, a value range of X is determined after big data statistical analysis, and a value of X is adjusted according to health conditions of the patient; adjusting the video movements of the exercise prescription of the user includes adjusting recommended high-intensity movements to medium-low intensity movements; the high-intensity movements that movements that cause the heart rate to exceed the upper limit of the target heart rate during exercise; and the medium-low intensity movements include movements that keep the heart rate within the target heart rate range during exercise.

Optionally, determining the target heart rate of the user being lower than the lower limit of the target heart rate range includes that a duration of the target heart rate being lower than the lower limit of the target heart rate in the whole-body exercise and a total duration of the whole-body exercise are counted after the user completes exercise once according to the video movements, the duration of the target heart rate being lower than the lower limit of the target heart rate in the whole-body exercise is divided by the total duration of the whole-body exercise, and if a result is greater than Y %, the system determines that the user has a target heart rate lower than the lower limit of the target heart rate range during exercise, a value range of Y is determined after big data statistical analysis, and a value of Y is adjusted according to health conditions of the patient; adjusting the video movements in the exercise prescription of the user includes adjusting recommended low-intensity movements to medium-high intensity movements; the low-intensity movements include movements that cause the heart rate to not reach the lower limit of the target heart rate during exercise; and the medium-high intensity movements include movements that keep the heart rate within the target heart rate range during exercise.

According to the specific embodiments provided by the present disclosure, the present disclosure discloses the following technical effects:

The present disclosure provides a movement adjustment system based on heart rates and RPE feedbacks of different users, including: a user client, a heart rate monitoring device, a server, and a doctor client. The user client includes an RPE self-rating module, an RPE data acquisition module, a user-side video movement display module, and a user-side data storage module. The heart rate monitoring device is worn on a user and includes an exercise data acquisition module. The server includes a data input module, a core processor, and a video movement library. The doctor client includes a doctor-side video movement display module, a video movement sending module, and a doctor-side data storage module. In the present disclosure, the client is not only an exercise rehabilitation execution platform, but also a data acquisition tool, and the server is not only a platform for data processing, but also a database for storing data. After different users complete exercise once according to the video movements of the exercise prescription, the present disclosure can make personalized adjustment to the exercise prescriptions of the users according to the too high or low heart rates of different users during exercise and the subjective RPE ratings of the users after the exercise. The personalized adjustment includes adjusting the target heart rate range and video movements in the exercise prescription of the user, so as to make the target heart rate and video movements in the exercise prescription recommended to the user more accurate and more applicable to the user, such that different users can obtain their own personalized target heart rate ranges and video movements, and the user can exercise more safely and effectively.

BRIEF DESCRIPTION OF THE DRAWINGS

To describe the technical solutions in embodiments of the present disclosure or in the prior art more clearly, the accompanying drawings required in the embodiments are briefly described below. Apparently, the accompanying drawings in the following description show merely some embodiments of the present disclosure, and other drawings can be derived from these accompanying drawings by those of ordinary skill in the art without creative efforts.

DETAILED DESCRIPTION OF THE EMBODIMENTS

The technical solution in the embodiments of the present disclosure will be described below clearly and completely with reference to the accompanying drawings in the embodiments of the present disclosure. Apparently, the described embodiments are merely some rather than all of the embodiments of the present disclosure. All other embodiments obtained by those of ordinary skill in the art based on the embodiments of the present disclosure without creative efforts shall fall within the protection scope of the present disclosure.

An objective of embodiments of the present disclosure is to provide a movement adjustment system based on heart rates and RPE feedbacks of different users, which adjusts movements of next exercise of a patient based on objective heart rate feedback of different users during exercise and subjective RPE feedback after the exercise, such that movement recommendation of an exercise prescription is more accurate and reasonable, and the patient can exercise more safely and effectively through personalized adjustment of the movements.

To make the above-mentioned objective, features, and advantages of the present disclosure clearer and more comprehensible, the present disclosure will be further described in detail below in conjunction with the accompanying drawings and specific embodiments.

Figure 1:
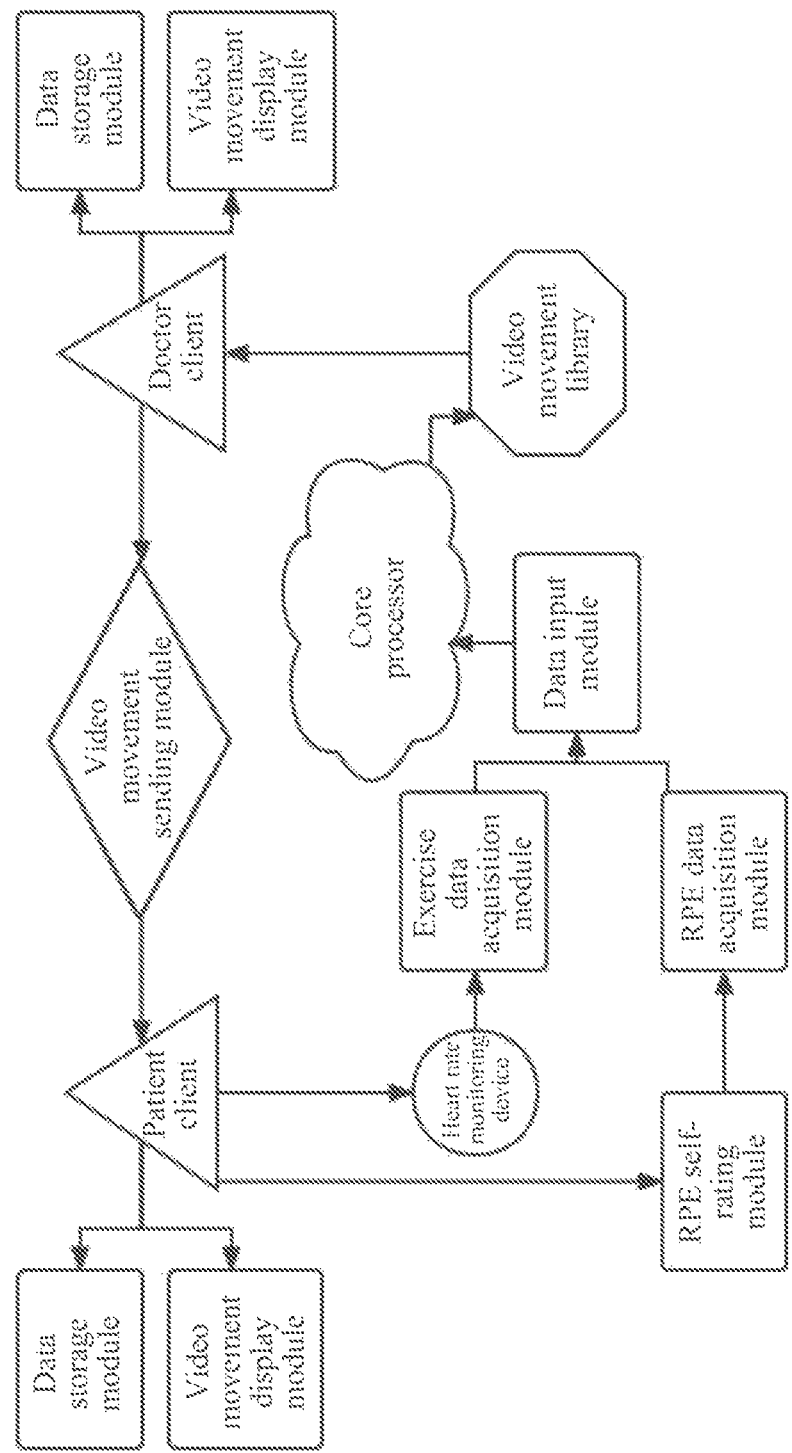
FIG. 1 is a schematic structural diagram of a movement adjustment system based on heart rates and RPE feedbacks of different users in an embodiment of the present disclosure.

As shown in FIG. 1, the above system in the present disclosure includes: a user client, a heart rate monitoring device, a server, and a doctor client.

The user client includes an RPE data acquisition module, an RPE self-rating module, a user-side video movement display module, and a user-side data storage module. The RPE data acquisition module, the RPE self-rating module, the user-side video movement display module, and the user-side data storage module are connected in sequence.

Specifically, the RPE self-rating module is configured to rate a difficulty of completing an exercise, after the user making the exercise. The difficulty includes: the difficulty of completing a movement by the user.

The RPE data acquisition module is configured to acquire RPE rating information of the user.

The user-side video movement display module is configured to display exercise movements of the user.

The user-side data storage module is configured to store the exercise movements of the user.

The heart rate monitoring device includes an exercise data acquisition module and is worn on a user. The exercise data acquisition module is connected with the RPE self-rating module.

The exercise data acquisition module is configured to acquire heart rate information of the user during exercise. The heart rate information includes a heart rate not reaching a lower limit of a target heart rate, a heart rate reaching a target heart rate range, and a heart rate exceeding an upper limit of the target heart rate during exercise.

The exercise data acquisition module includes, but is not limited to, a heart rate band, watch, and bracelet, and completes exercise evaluation under the guidance of the movements in the exercise test video sent with the doctor's confirmation.

The server includes a data input module, a core processor, and a video movement library. The input module is connected with the exercise data acquisition module and the core processor, and the core processor is connected with the video movement library.

The data input module is configured to input the heart rate information and the RPE rating information of the user during exercise into the core processor.

The core processor is configured to select exercise movements suitable for the user from the video movement library according to the heart rate information and the RPE rating information of the user during exercise, replace movements not suitable for the user in an original exercise prescription, generate movements for a new exercise prescription, and send the movements for the new exercise prescription to the doctor client.

Specifically, the core processor includes: a heart rate information processing sub-module, a duration recording sub-module, a too-high target heart rate processing sub-module, a too-low target heart rate processing sub-module, a too-high RPE rating processing sub-module, a too-low RPE rating processing sub-module, and a heart rate and RPE feedback collaborative processing sub-module.

The heart rate information processing sub-module is configured to process different exercise stages at which heart rate changes of the user during exercise are. The heart rate changes include not reaching a target heart rate, reaching the target heart rate, and exceeding the target heart rate. The exercise stages include a warm-up exercise stage, a whole-body exercise stage, a cooling-down exercise stage, and a stretching exercise stage.

The duration recording sub-module is connected with the heart rate information processing sub-module, and the duration recording sub-module is configured to record durations of different exercise stages at which the heart rate changes of the user during exercise are. The durations include durations of not reaching the target heart rate, reaching the target heart rate, and exceeding the target heart rate in the warm-up exercise stage, durations of not reaching the target heart rate, reaching the target heart rate, and exceeding the target heart rate in the whole-body exercise stage, durations of not reaching the target heart rate, reaching the target heart rate, and exceeding the target heart rate in the cooling-down exercise stage, and durations of not reaching the target heart rate, reaching the target heart rate, and exceeding the target heart rate in the stretching exercise stage.

Figure 2:
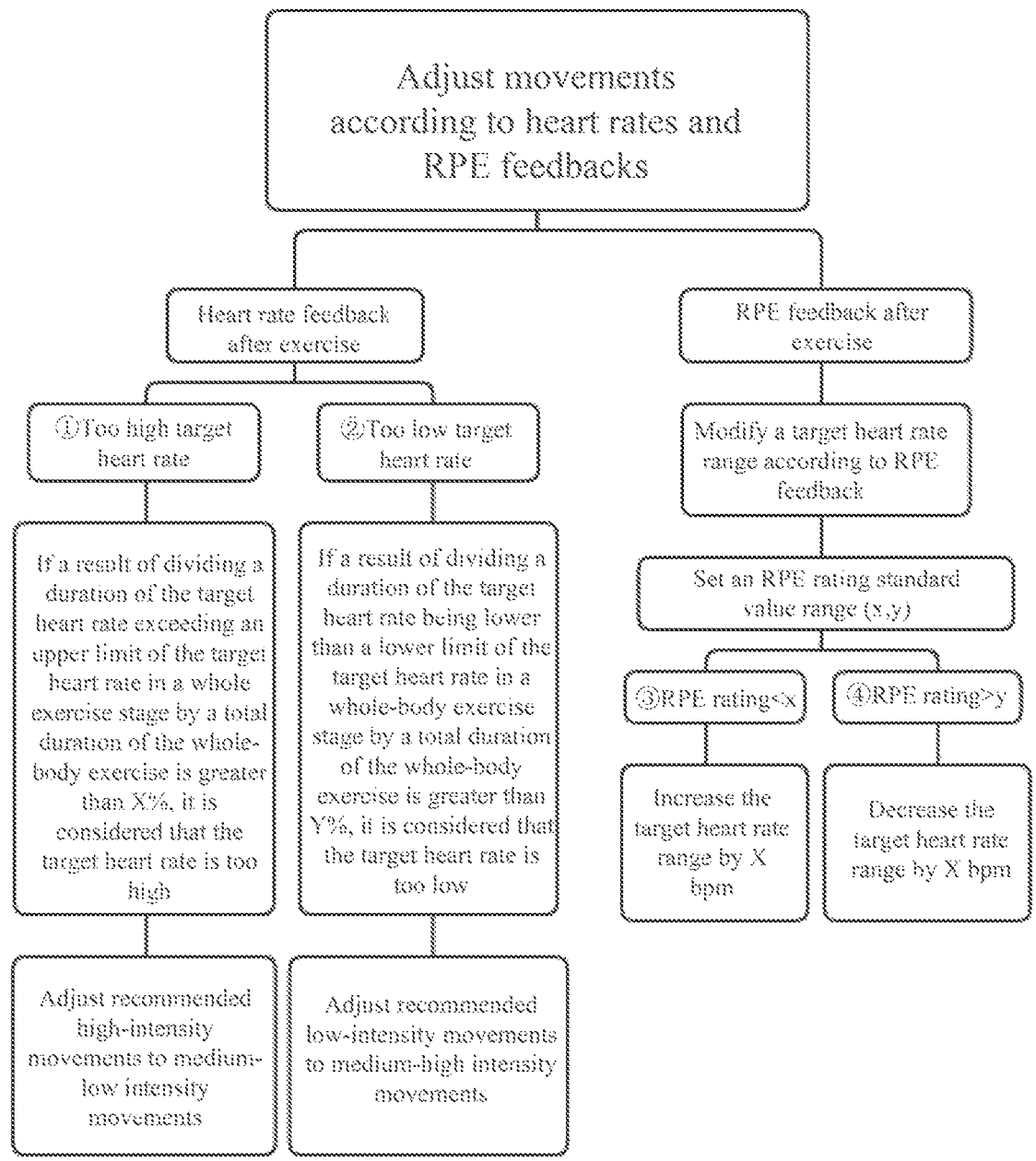
FIG. 2 is a flow chart of a processing method of a too-high target heart rate processing sub-module and a too-low target heart rate processing sub-module in the embodiment of the present disclosure.

As shown in FIG. 2, the too-high target heart rate processing sub-module is connected with the heart rate information processing sub-module, and the too-high target heart rate processing sub-module is configured to adjust video movements of an exercise prescription of the user when a target heart rate of the user during exercise is too high. Determining the target heart rate of the user being too high includes that a duration of the target heart rate exceeding the upper limit of the target heart rate in a whole exercise stage and a total duration of the whole-body exercise are counted after the user completes exercise once according to the video movements, the duration of the target heart rate exceeding the upper limit of the target heart rate in the whole exercise stage is divided by the total duration of the whole-body exercise, and if a result is greater than X %, the system determines that the user has a too high target heart rate during exercise, a value range of X is determined after big data statistical analysis, and a value of X is adjusted according to health conditions of the patient. Adjusting the video movements of the exercise prescription of the user includes adjusting recommended high-intensity movements to medium-low intensity movements. The high-intensity movements include movements that cause the heart rate to exceed the upper limit of the target heart rate during exercise. The medium-low intensity movements include movements that keep the heart rate within the target heart rate range during exercise.

As shown in FIG. 2, the too-low target heart rate processing sub-module is connected with the heart rate information processing sub-module, and the too-low target heart rate processing sub-module is configured to adjust the video movements of the exercise prescription of the user when the target heart rate of the user during exercise is too low. Determining the target heart rate of the user being too low includes that a duration of the target heart rate being lower than the lower limit of the target heart rate in the whole-body exercise and a total duration of the whole-body exercise are counted after the user completes exercise once according to the video movements, the duration of the target heart rate being lower than the lower limit of the target heart rate in the whole-body exercise is divided by the total duration of the whole-body exercise, and if a result is greater than Y %, the system determines that the user has a too low target heart rate during exercise, a value range of Y is determined after big data statistical analysis, and a value of Y is adjusted according to health conditions of the patient. Adjusting the video movements of the exercise prescription of the user includes adjusting recommended low-intensity movements to medium-high intensity movements. The low-intensity movements include movements that cause the heart rate to not reach the lower limit of the target heart rate during exercise. The medium-high intensity movements include movements that keep the heart rate within the target heart rate range during exercise.

The too-high RPE rating processing sub-module is connected with the RPE self-rating module, the too-high RPE rating processing sub-module is configured to set an RPE rating standard value range (x,y) according to different user conditions, and when an RPE rating is greater than y after the user completes exercise once, a target heart rate range of a patient is decreased by X bpm. The different user conditions include an age, gender, and health status of the user. The health status includes disease diagnosis and duration of illness.

The too-low RPE rating processing sub-module is connected with the RPE self-rating module, the too-low RPE rating processing sub-module is configured to set the RPE rating standard value range (x,y) according to different user conditions, and when the RPE rating is less than x after the user completes exercise once, the target heart rate range of the patient is increased by X bpm. The different user conditions include the age, gender, and health status of the user. The health status includes disease diagnosis and duration of illness.

Figure 3:
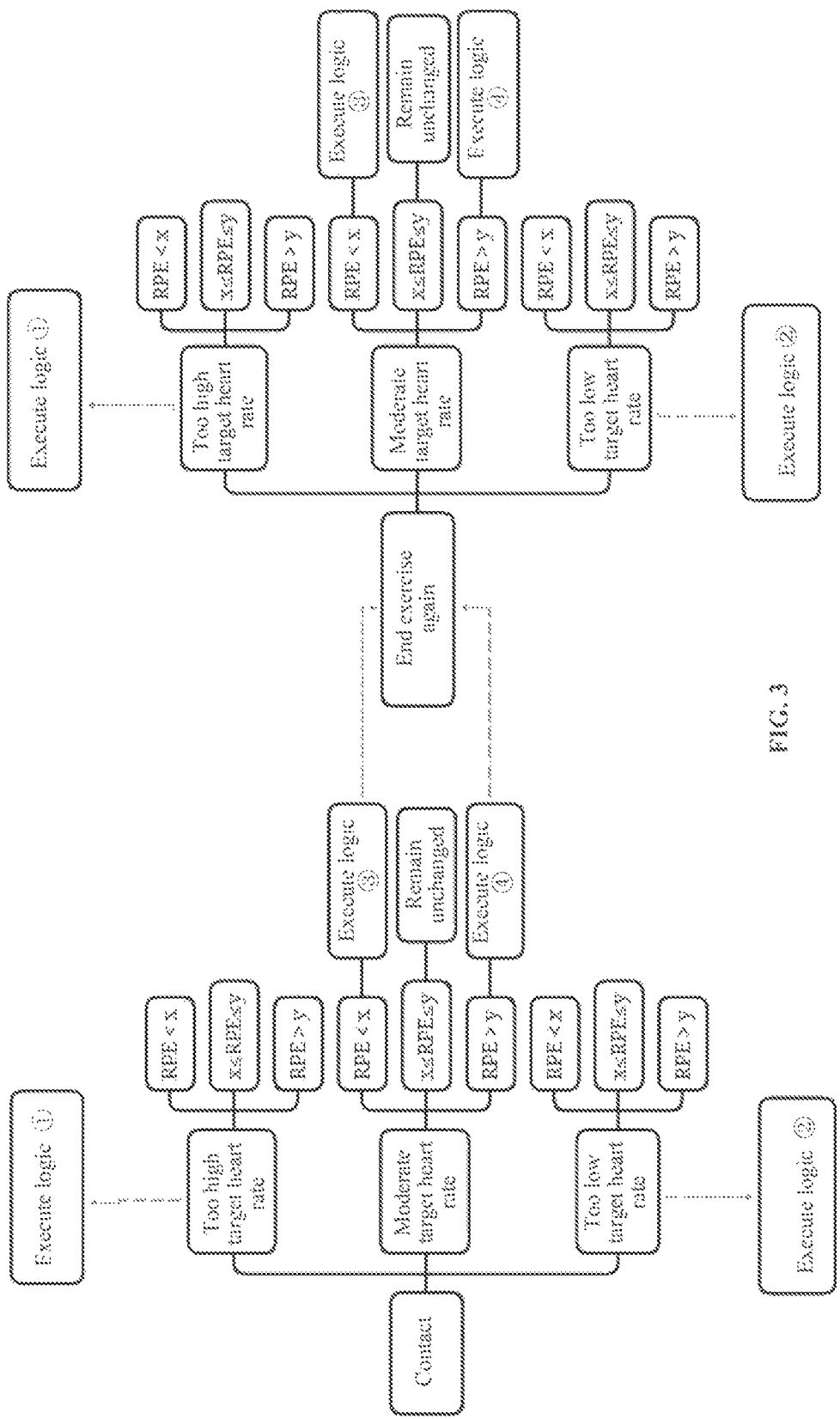
FIG. 3 is a flow chart of processing by a heart rate and RPE feedback collaborative processing sub-module in the embodiment of the present disclosure.

As shown in FIG. 3, the heart rate and RPE feedback collaborative processing sub-module is connected with the too-low RPE rating processing sub-module and the too-high RPE rating processing sub-module, and the heart rate and RPE feedback collaborative processing sub-module is configured to adjust the video movements of the exercise prescription under simultaneous or non-simultaneous abnormalities of the heart rates and the RPE feedbacks of the different users during exercise. The simultaneous or non-simultaneous abnormalities include that the target heart rate being too high matches any one of RPE<x, x≤RPE≤y, and RPE>y, the target heart rate being within the target heart rate range matches any one of RPE<x, x≤RPE≤y, and RPE>y, and the target heart rate being too low matches any one of RPE<x, x≤RPE≤y, and RPE>y. After the user completes exercise once according to the video movements, when the target heart rate is abnormally too high or too low, the heart rate and RPE feedback collaborative processing sub-module performs processing according to a condition where the target heart rate is too high or too low. The processing includes transferring a processing task to the too-high target heart rate processing sub-module or the too-low target heart rate processing sub-module for processing, and in this case an abnormal RPE feedback is not processed. The abnormal RPE feedback includes RPE<x or RPE>y. When the target heart rate is within the target heart rate range and the RPE rating meets RPE<x or RPE>y, the heart rate and RPE feedback collaborative processing sub-module transfers a processing task to the too-low RPE rating processing sub-module or the too-high RPE rating processing sub-module for processing. When the target heart rate is within the target heart rate range and the RPE rating meets x≤RPE≤y, the exercise of the user is regarded as ideal, without movement adjustment being performed.

The doctor client includes a doctor-side video movement display module, a video movement sending module, and a doctor-side data storage module. The doctor-side video movement display module is connected with the exercise data acquisition module and the video movement sending module, and the video movement sending module is connected with the doctor-side data storage module.

The doctor-side video movement display module is configured to display video movements at the doctor client.

The video movement sending module is configured to send the video movements from the doctor client to the user client.

The following describes the use process for the user, which is specifically as follows.

Step 1: The user downloads a patient client app, logs in and registers with a mobile phone number, and fills in a health questionnaire.

Step 2: The user wears a heart rate monitoring device including but not limited to a heart rate band, watch and bracelet, and completes exercise evaluation under the guidance of the movements in the exercise test video sent with the doctor's confirmation.

Step 3: After the user completes the exercise evaluation, the system intelligently recommends an exercise prescription suitable for the user to the doctor client according to the evaluation result. The doctor checks and confirms video movements in the doctor-side video movement display module. After confirmation, the doctor clicks "Send", and then the video movements are sent to the patient client through the video movement sending module.

Step 4: The user refreshes the patient client and receives the exercise prescription issued by the doctor, and the video movements are displayed in the video movement display module of the patient client. The user can click "Start Exercise" when wearing the heart rate monitoring device, and then makes exercise according to the video movements.

Step 5: After the user completes exercise once under the guidance of the video movements, the exercise data acquisition module can acquire data in the exercise.

Step 6: After the user completes exercise once under the guidance of the video movements, the RPE data acquisition module can acquire the RPE rating of this exercise.

Step 7: The exercise data acquisition module acquires data in the exercise, which is derived from the heart rate monitored by the heart rate monitoring device, including but not limited to a heart rate of the user completing a single movement and a duration at that heart rate, a heart rate of completing a warm-up exercise and a duration at that heart rate, a heart rate of completing a whole-body exercise and a duration at that heart rate, a heart rate of completing a cooling-down exercise and a duration at that heart rate, and a heart rate of completing a stretching exercise and a duration at that heart rate. For example, the duration of completing the single movement at 80 bpm is 10 min, the duration of completing the single movement at 130 bpm is 5 min, and the duration of completing the single movement at 170 bpm is 1 min. The duration of completing the warm-up exercise at 100 bpm is 5 min. The duration of completing the whole-body exercise at 105 bpm is 20 min, the duration of completing the whole-body exercise at 140 bpm was 30 min, and the duration of completing the whole-body exercise at 160 bpm is 10 min. The duration of completing the cooling-down exercise at 160 bpm is 5 min, and the duration of completing the cooling-down exercise at 110 bpm is 5 min. The duration of completing the stretching exercise at 90 bpm is 10 min, etc.

Step 8: The RPE data acquisition module acquires the RPE rating of this exercise, which is derived from the self-rating of the user through the RPE self-rating module on the patient client. The RPE rating ranges from 1 to 10 points, "1" means no effort, and "10" means extreme effort. For example, after the user completes exercise once, the RPE self-rating is 5 points, which means appropriate.

Step 9: The data acquired by the exercise data acquisition module and the RPE data acquisition module is transmitted to the core processor through the data input module.

Step 10: The core processor analyzes and processes data using the following logics, including the following sub-steps.

Step 101: The collected durations of different heart rates in each stage of exercise are counted.

Step 102: A duration of the target heart rate exceeding the upper limit of the target heart rate in the whole exercise stage and a total duration of the whole-body exercise are counted, the duration of the target heart rate exceeding the upper limit of the target heart rate in the whole exercise stage is divided by the total duration of the whole-body exercise, and if a result is greater than X %, the system determines that the user has a too high target heart rate during exercise, a value range of X is determined after big data statistical analysis, and a value of X is adjusted according to health conditions of the patient. X is a two-place decimal such as 11% and 12%. For example, the user is 20 years old, male, in a sub-health status, loves exercise at normal times and has no other adverse health conditions. It is determined the target heart rate is too high as 20%, the target heart rate range is (120,160), and the heart rate during exercise exceeding 160 bpm is considered to exceed the upper limit of the target heart rate. After the exercise, the duration of the target heart rate exceeding 160 bpm in the whole exercise stage is counted as 10 min, and the total duration of the whole-body exercise is counted as 30 min. The duration of the target heart rate exceeding the upper limit of the target heart rate in the whole exercise stage divided by the total duration of the whole-body exercise is equal to 10/30=33%. As 33%>20%, the system determines that the target heart rate of the user during exercise is too high.

Step 103: A duration of the target heart rate being lower than the lower limit of the target heart rate in the whole-body exercise and a total duration of the whole-body exercise are counted, the duration of the target heart rate being lower than the lower limit of the target heart rate in the whole-body exercise is divided by the total duration of the whole-body exercise, and if a result is greater than Y %, the system determines that the user has a too low target heart rate during exercise, a value range of Y is determined after big data statistical analysis, and a value of Y is adjusted according to health conditions of the patient. Y is a two-place decimal such as 31% and 32%. For example, the user is 20 years old, male, in a sub-health status, loves exercise at normal times and has no other adverse health conditions. It is determined that the target heart rate is too low as 30%, the target heart rate range is (120,160), and the heart rate during exercise being lower than 120 bpm is considered to be lower than the lower limit of the target heart rate. After the exercise, the duration of the target heart rate being lower than 120 bpm in the whole-body exercise is counted as 10 min, and the total duration of the whole-body exercise is counted as 30 min. The duration of the target heart rate being lower than the lower limit of the target heart rate in the whole-body exercise divided by the total duration of the whole-body exercise is equal to 10/30=33%. As 33%>30%, the system determines that the target heart rate of the user during exercise is too low.

Step 104: RPE ratings after exercise are counted, and an RPE rating standard value range (x,y) is set. If the RPE rating is within the standard value range, it is considered that the subjective feeling of exercise is moderate. The value range of (x,y) is 3<x and y<8, and x and y are integers.

Step 105: If the RPE rating is less than x, the target heart rate range is increased by X bpm, a value range of X is 5<X<10, and X is an integer. For example, the user is 20 years old, male, in a sub-health status, loves exercise at normal times and has no other adverse health conditions. The target heart rate range is (120,160). After the exercise, the RPE value (4, 7) is considered moderate. After one exercise, the RPE self-rating is 2 points. Since 2 is less than 4, it is considered that the RPE rating is low. At this time, the target heart rate range can be increased by 5 bpm, and the target heart rate range of the user in the next exercise is adjusted to (125,165).

Step 106: If the RPE rating is greater than y, the target heart rate range is decreased by X bpm, a value range of X is 5<X<10, and X is an integer. For example, the user is 20 years old, male, in a sub-health status, loves exercise at normal times and has no other adverse health conditions. The target heart rate range is (120,160). After the exercise, the RPE value (4, 7) is considered moderate. After one exercise, the RPE self-rating is 9 points. Since 9 is greater than 7, it is considered that the RPE rating is high. At this time, the target heart rate range can be decreased by 5 bpm, and the target heart rate range of the user in the next exercise is adjusted to (115,155).

Step 107: After the user completes exercise once according to the video movements, the system safely controls the exercise of the user from both subjective and objective perspectives. The data of heart rate and the duration of the heart rate collected by the system are considered objective. When the user fills in the RPE rating after exercise, it is regarded as subjective. A principle is that when the subjective and objective rating results are contradictory, the objective data is selected for adjustment. This principle is not applicable to patients with cardiovascular disease who use drugs to slow down the heart rate.

Step 108: The user applies the conditions in step 107. When the user executes the logic in step 102 and determines that the target heart rate is too high, the recommended high-intensity movements are adjusted to medium-low intensity movements.

Step 109: The user applies the conditions in step 107. When the user executes the logic in step 103 and determines that the target heart rate is too low, the recommended low-intensity movements are adjusted to medium-high intensity movements.

Step 110: When the target heart rate of the user is within a target heart rate range recommended by the doctor, and the RPE rating of the user after the exercise is less than the recommended lower limit of the RPE rating, the logic in step 105 is executed.

Step 111: When the target heart rate of the user is within the target heart rate range recommended by the doctor, and the RPE rating of the user after the exercise is greater than the recommended upper limit of the RPE rating, the logic in step 106 is executed.

Step 112: When the user executes the logic in step 105 and increases the target heart rate range by X bpm, after the user completes the next exercise according to the video movements, the logic in step 103 occurs and it is determined that the target heart rate is too low. At this time, the recommended low-intensity movements are adjusted to medium-high intensity movements.

Step 113: When the user executes the logic in step 106 and decreases the target heart rate range by X bpm, after the user completes the next exercise according to the video movements, the logic in step 102 occurs and it is determined that the target heart rate is too high. At this time, the recommended high-intensity movements are adjusted to medium-low intensity movements.

After processing by the processing logic, the core processor selects the movements with required intensity from the movement library according to the processing results, and recommends the selected movements to the doctor client. The doctor checks and confirms video movements in the doctor-side video movement display module. After confirmation, the doctor sends the video movements by a click, and the video movements are sent to the patient client through the video movement sending module. In addition, the sent video movements are stored in the doctor-side data storage module.

The patient client receives the video movements sent by the doctor client and clicks to start exercise. The video movements are displayed in the video movement display module of the patient client. After the user completes the exercise according to the video movements, the exercise data is stored in the data storage module of the patient client, and transmitted back to the core processor through the acquisition module and input module, so as to facilitate the next processing.

Through the above design, the present disclosure adjusts the movement video of the exercise of the user from the subjective and objective perspectives, effectively improving the accuracy of the movement video recommendation, so as to help the user avoid the existing problems of poor exercise effect caused by blind movement or injury to the body caused by excessive exercise intensity, so as to make the exercise more safe and effective and achieve scientific exercise.

Embodiments of the present specification are described in a progressive manner, each embodiment focuses on the difference from other embodiments, and the same and similar parts between the embodiments may refer to each other. Since the system disclosed in an embodiment corresponds to the method disclosed in another embodiment, the description is relatively simple, and reference can be made to the method description.

In this specification, some specific embodiments are used for illustration of the principles and implementations of the present disclosure. The description of the foregoing embodiments is used to help illustrate the method of the present disclosure and the core ideas thereof. In addition, those of ordinary skill in the art can make various modifications in terms of specific implementations and the scope of application in accordance with the ideas of the present disclosure. In conclusion, the content of this specification shall not be construed as limitations to the present disclosure.

What is claimed is:

1. A movement adjustment system based on heart rates and rating of perceived exertion (RPE) feedbacks of different users, comprising:

a user client, a heart rate monitoring device, a server, and a doctor client, wherein the user client comprises an RPE data acquisition module, an RPE self-rating module, a user-side video movement display module, and a user-side data storage module; and the RPE data acquisition module, the RPE self-rating module, the user-side video movement display module, and the user-side data storage module are connected in sequence;

the heart rate monitoring device comprises an exercise data acquisition module and is worn on a user; and the exercise data acquisition module is connected with the RPE self-rating module;

the server comprises a data input module, a core processor, and a video movement library; and the input module is connected with the exercise data acquisition module and the core processor, and the core processor is connected with the video movement library;

the doctor client comprises a doctor-side video movement display module, a video movement sending module, and a doctor-side data storage module; and the doctor-side video movement display module is connected with the exercise data acquisition module and the video movement sending module, and the video movement sending module is connected with the doctor-side data storage module;

the core processor specifically comprises: a heart rate information processing sub-module, a duration recording sub-module, a too-high target heart rate processing sub-module, a too-low target heart rate processing sub-module, a too-high RPE rating processing sub-module, a too-low RPE rating processing sub-module, and a heart rate and RPE feedback collaborative processing sub-module;

the heart rate information processing sub-module is configured to process different exercise stages at which heart rate changes of the user during exercise are; the heart rate changes comprise not reaching a target heart rate, reaching the target heart rate, and exceeding the target heart rate; and the exercise stages comprise a warm-up exercise stage, a whole-body exercise stage, a cooling-down exercise stage, and a stretching exercise stage;

the duration recording sub-module is connected with the heart rate information processing sub-module, and the duration recording sub-module is configured to record durations of different exercise stages at which the heart rate changes of the user during exercise are; and the durations comprise durations of not reaching the target heart rate, reaching the target heart rate, and exceeding the target heart rate in the warm-up exercise stage, durations of not reaching the target heart rate, reaching the target heart rate, and exceeding the target heart rate in the whole-body exercise stage, durations of not reaching the target heart rate, reaching the target heart rate, and exceeding the target heart rate in the cooling-down exercise stage, and durations of not reaching the target heart rate, reaching the target heart rate, and exceeding the target heart rate in the stretching exercise stage;

the too-high target heart rate processing sub-module is connected with the heart rate information processing sub-module, and the too-high target heart rate processing sub-module is configured to adjust video movements in an exercise prescription of the user when a target heart rate of the user during exercise exceeds an upper limit of a target heart rate range;

the too-low target heart rate processing sub-module is connected with the heart rate information processing sub-module, and the too-low target heart rate processing sub-module is configured to adjust the video movements in the exercise prescription of the user when the target heart rate of the user during exercise is lower than a lower limit of the target heart rate range;

the too-high RPE rating processing sub-module is connected with the RPE self-rating module, the too-high RPE rating processing sub-module is configured to set an RPE rating standard value range (x,y) according to different user conditions, and when an RPE rating is greater than y after the user completes exercise once, a target heart rate range of a patient is decreased by X bpm; the different user conditions comprise an age, gender, and health status of the user; and the health status comprises disease diagnosis and duration of illness;

the too-low RPE rating processing sub-module is connected with the RPE self-rating module, the too-low RPE rating processing sub-module is configured to set the RPE rating standard value range (x,y) according to different user conditions, and when the RPE rating is less than x after the user completes exercise once, the target heart rate range of the patient is increased by X bpm; the different user conditions comprise the age, gender, and health status of the user; and the health status comprises disease diagnosis and duration of illness; and the heart rate and RPE feedback collaborative processing sub-module is connected with the too-low RPE rating processing sub-module and the too-high RPE rating processing sub-module, and the heart rate and RPE feedback collaborative processing sub-module is configured to adjust the video movements in the exercise prescription under simultaneous or non-simultaneous abnormalities of the heart rates and the RPE feedbacks of the different users during exercise; the simultaneous or non-simultaneous abnormalities comprise that the target heart rate being too high matches any one of RPE<x, x≤RPE≤y, and RPE>y, the target heart rate being within the target heart rate range matches any one of RPE<x, x≤RPE≤y, and RPE>y, and the target heart rate being too low matches any one of RPE<x, x≤RPE≤y, and RPE>y; after the user completes exercise once according to the video movements, when the target heart rate is abnormally too high or too low, the heart rate and RPE feedback collaborative processing sub-module performs processing according to a condition where the target heart rate is too high or too low; the processing comprises transferring a processing task to the too-high target heart rate processing sub-module or the too-low target heart rate processing sub-module for processing, and an abnormal RPE feedback is not processed; the abnormal RPE feedback comprises RPE<x or RPE>y; when the target heart rate is within the target heart rate range and the RPE rating meets RPE<x or RPE>y, the heart rate and RPE feedback collaborative processing sub-module transfers a processing task to the too-low RPE rating processing sub-module or the too-high RPE rating processing sub-module for processing; and when the target heart rate is within the target heart rate range and the RPE rating meets x≤RPE≤y, an exercise of the user is regarded as ideal, without movement adjustment being performed.

2. The movement adjustment system according to claim 1, wherein the RPE self-rating module is configured to rate difficulty of completing exercise after the exercise by the user;
the RPE data acquisition module is configured to acquire RPE rating information of the user;
the user-side video movement display module is configured to display exercise movements of the user; and
the user-side data storage module is configured to store the exercise movements of the user.

3. The movement adjustment system according to claim 1, wherein the exercise data acquisition module is configured to acquire heart rate information of the user during exercise; and the heart rate information comprises a heart rate not reaching a lower limit of a target heart rate during exercise, a heart rate reaching a target heart rate range, and a heart rate exceeding an upper limit of the target heart rate.

4. The movement adjustment system according to claim 3, wherein the data input module is configured to input the heart rate information and the RPE rating information of the user during exercise into the core processor; and
the core processor is configured to select exercise movements suitable for the user from the video movement library according to the heart rate information and the RPE rating information of the user during exercise, replace movements not suitable for the user in an original exercise prescription, generate movements for a new exercise prescription, and send the movements for the new exercise prescription to the doctor client.

5. The movement adjustment system according to claim 4, wherein the doctor-side video movement display module is configured to display video movements in the doctor client; and
the video movement sending module is configured to send the video movements from the doctor client to the user client.

6. The movement adjustment system according to claim 1, wherein determining the target heart rate of the user being higher than the upper limit of the target heart rate range comprises that a duration of the target heart rate exceeding the upper limit of the target heart rate in a whole exercise stage and a total duration of the whole-body exercise are counted after the user completes exercise once according to the video movements, the duration of the target heart rate exceeding the upper limit of the target heart rate in the whole exercise stage is divided by the total duration of the whole-body exercise, and if a result is greater than X %, the system determines that the user has a target heart rate higher than the upper limit of the target heart rate range during exercise, a value range of X is determined after big data statistical analysis, and a value of X is adjusted according to health conditions of the patient; adjusting the video movements of the exercise prescription of the user comprises adjusting recommended high-intensity movements to medium-low intensity movements; the high-intensity movements comprise movements that cause the heart rate to exceed the upper limit of the target heart rate during exercise; and the medium-low intensity movements comprise movements that keep the heart rate within the target heart rate range during exercise.

7. The movement adjustment system according to claim 1, wherein determining the target heart rate of the user being lower than the lower limit of the target heart rate range comprises that a duration of the target heart rate being lower than the lower limit of the target heart rate in the whole-body exercise and a total duration of the whole-body exercise are counted after the user completes exercise once according to the video movements, the duration of the target heart rate being lower than the lower limit of the target heart rate in the whole-body exercise is divided by the total duration of the whole-body exercise, and if a result is greater than Y %, the system determines that the user has a target heart rate lower than the lower limit of the target heart rate range during exercise, a value range of Y is determined after big data statistical analysis, and a value of Y is adjusted according to health conditions of the patient; adjusting the video movements in the exercise prescription of the user comprises adjusting recommended low-intensity movements to medium-high intensity movements; the low-intensity movements comprise movements that cause the heart rate to not reach the lower limit of the target heart rate during exercise; and the medium-high intensity movements comprise movements that keep the heart rate within the target heart rate range during exercise.

* * * * *